United States Patent [19]
Earl

[11] Patent Number: 5,277,647
[45] Date of Patent: Jan. 11, 1994

[54] SYSTEM FOR MASS PRODUCTION AND CONSUMPTION OF HONEY

[75] Inventor: Gregory K. Earl, Arlington, Va.

[73] Assignee: American Apiary Farm Company, Arlington, Va.

[21] Appl. No.: 946,572

[22] Filed: Sep. 18, 1992

[51] Int. Cl.⁵ .............................................. A01K 59/00
[52] U.S. Cl. ...................................................... 449/2
[58] Field of Search ............... 449/1, 2, 27; 47/58, 47/58.01

[56] References Cited

U.S. PATENT DOCUMENTS

| | | | |
|---|---|---|---|
| 4,077,157 | 3/1978 | Bradner | 47/58 |
| 4,114,315 | 9/1978 | Rinella | 47/61 |
| 4,346,490 | 8/1982 | Katz et al. | 449/2 |
| 4,402,099 | 9/1983 | Platt, Jr. | 6/1 |
| 4,425,136 | 1/1984 | Pearson et al. | 44/51 |
| 4,491,994 | 1/1985 | Youssef | 6/1 |
| 5,038,518 | 8/1991 | Davis | 47/58 |

FOREIGN PATENT DOCUMENTS

| | | | |
|---|---|---|---|
| 760915 | 9/1980 | U.S.S.R. | 449/27 |
| 969218 | 11/1982 | U.S.S.R. | 449/1 |

Primary Examiner—Robert P. Swiatek
Attorney, Agent, or Firm—Longacre & White

[57] ABSTRACT

The present disclosure concerns a system for combining the reforestation of cleared land with a bee pasture, mass production of honey, and fermentation of honey for the distillation of fuel alcohol to obtain a renewable source of clean, efficient energy.

1 Claim, 3 Drawing Sheets

SYSTEM FOR MASS PRODUCTION AND CONSUMPTION OF HONEY

BACKGROUND OF THE INVENTION a) Field of the Invention

The invention concerns a system for the mass production of honey. In addition, the invention concerns a system for the reforestation of cleared land and the production of fuel alcohol.

b) Description of Related Art

Honey is still obtained in the known historical manner. Namely, flowering flora provides a source of nectar for bees which convert the nectar to honey. The three factors which affect the honey obtained are:

1) the quantity of nectar available at a given time;
2) the quality of the nectar available at the given time; and
3) the duration of the given time in which nectar is available.

The first factor limits the size of a bee colony which may be supported by the nectar, i.e. a larger quantity of available nectar will support a larger colony of bees, which in turn will generally produce greater quantities of honey. The second factor limits the quality of the honey which is obtained, e.g. table grade or bakery grade. The third factor limits the periods of the year in which honey is obtained (honey is consumed by the bees during periods of the year in which nectar is not available).

There are generally three nectar periods of the year during which nectar is available. The first nectar period occurs when dandelions, fruit trees and spring wildflowers are flowering. The second, and generally most prolific nectar period occurs when clover, sweetclover and alfalfa are flowering. The third nectar period occurs when goldenrod and aster are flowering. At all other times of the year, the bees must be sustained by reserves of honey which are contained in the colonies. Generally speaking, the geographic areas in which the nectar periods of the year occur are sufficiently separated such that:

1) the bees are not able to take advantage of one or more of the nectar periods;
2) the bees must be transported to a geographic area experiencing one of the nectar periods; or
3) the bees consume most of the nectar flying to and from a geographic area experiencing one of the nectar periods.

In practice, the bees are generally transported to geographic areas experiencing one of the nectar periods for the additional purpose of pollinating the flowering crops of a landowner. It is not uncommon for a beekeeper to generate more revenue by providing pollination services to a landowner than from the honey obtained during the nectar period.

With regard to a further aspect of the present invention, it is known that large areas of land have been commercially cleared, stripping the land of its valuable flora, and generally leaving little more than a collection of access and service roads. At present, known reforestation projects are long term, commercially unprofitable ventures, usually mandated by regulation intended to protect the environment, sometimes referred to as "green laws". Consequently, an unprotected indigenous population is often left with little or no means for generating revenue from the land once it has been cleared.

With regard to yet another aspect of the present invention, it is known that fuel alcohol may provide an efficient, clean source of fuel. Conventionally, various grains, molasses or sugar cane are used as a source of raw material for fermentation into fuel alcohol. However, the process for converting grain to fuel alcohol is generally not cost effective when considering more conventional processes, e.g. refining gasoline.

SUMMARY OF THE INVENTION

An objective of the present invention is to provide a system for addressing each of the aforementioned aspects. In particular, the present invention discloses a system for reforesting cleared land with a pasture of perennially flowering flora. Bee colonies are also introduced among the flora. In so far as the flora provides an abundant, year-round source of quality pasture and nectar for the bees, the quantity of honey which may be obtained per acre of land per year is far in excess of that which may be obtained by the known historical methods. The mass production of honey obtained according to the present invention may then be used to provide a continuous source of sugar for fermentation into fuel alcohol. Because the sugar is already in liquid form, fermentation of honey into fuel alcohol is easily accomplished by the distillation process which has been known since antiquity.

Another object of the present invention is to provide a system for the production of honey which is independent from seasonal changes.

A further object of the present invention is to provide a system for the reforestation of cleared land which is commercially profitable, as well as socially and environmentally responsible. The system according to the present invention provides a renewable fuel source which enables domestic independence from imported fuel sources, provides more efficient combustion than gasoline and produces fewer, less toxic emissions.

Yet another object of the present invention is to provide a system which promotes the synergistic effects of combining the reforestation of cleared land, the mass production of honey, and the mass inoculation of honey with yeast for fermentation of the honey to produce fuel alcohol. Different aspects of the present invention cooperatively fulfill several long felt needs. In particular, matching the continuous source of honey obtained through the coordination of perennially flowering flora and bee colonies, with the efficient distillation into fuel alcohol made possible by virtue of the sugar being provided in liquid form.

DESCRIPTION OF THE PREFERRED EMBODIMENT

Figure 1:
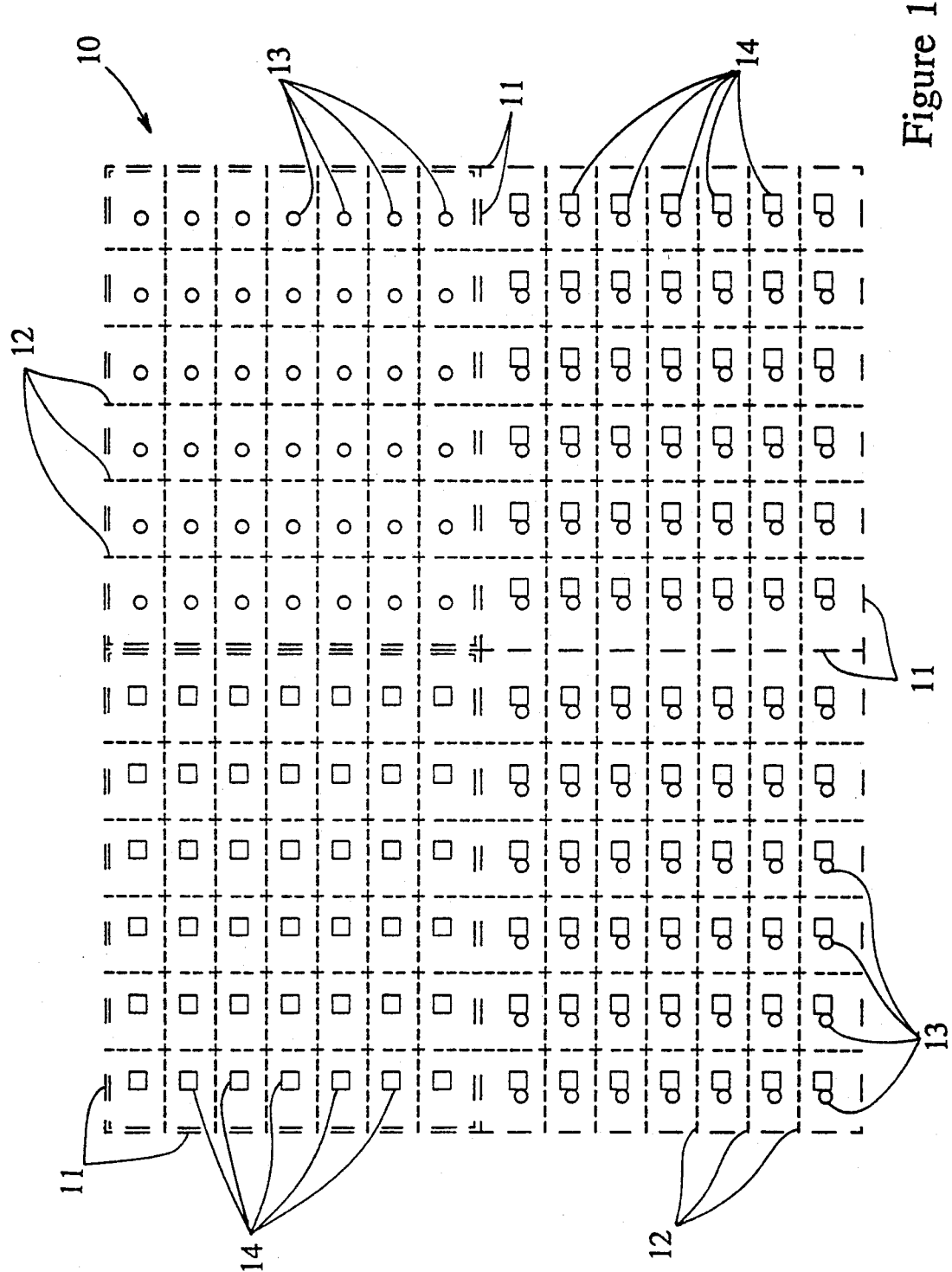
FIG. 1 shows a typical pasture for the reforestation of cleared land according to the present invention.

FIG. 1 shows a parcel of land 10 upon which a method according to the present invention is practiced. The parcel of land 10 is located in a region which has favorable climate and soil conditions, preferably in a region having a semi-arid, semi-tropical, other climate therebetween. The indigenous flora is cleared off the land, such as occurs during harvesting lumber by clear cutting methods, by fire as a consequence of nature or man, or simply because the indigenous flora does not sustain the indigenous population.

The present invention is particularly well suited for use in deforested areas which have been clear cut. Generally speaking, the known lumbering techniques leave the parcel of land 10 substantially cleared with a collection of access roads 11 and service roads 12. The access roads 11 provide means for transporting heavy loads by large trucks to and from a general area. The service roads 12 provide means for servicing the general area with a grid of smaller, less improved roads. Such a parcel of land is readily adapted to the present invention. The access roads 11 are used according to the present invention to transport seeds or seedlings, bee colonies, extraction equipment and distillation equipment to the parcel of land 10, as well as to transport honey and fuel alcohol from the parcel of land 10. The service roads 12 are used according to the present invention to distribute and maintain the flora and the bee colonies, as well as collect honey from the bee colonies. At a remote location from the parcel of land 10, approximately 2½-3 miles from the site of the bee colonies 14, a large scale extraction and distillation plant 20 is assembled, preferably located adjacent to an access road 11.

Flora which may be grouped together for the purpose of providing perennial flowering include: sweetgum (*Liquidamber Styraciflua*), Siberian pee shrub (*Caragana Arborecens*), Russian olive (*Elaeagnus Angustifolia*), tatarian honey suckle (*Lonicera Tataricia*), amur maple (*Acer Ginalla*), Peking cotton easter (*Cotton Easter Acutifolia*), autumn olive (*Eleagnus Umbella*), summer lilac (*Vitex Negundo*), American basswood (*Tilia Americana*), little leaf linden (*Tilia Cordata*), golden raintree (*Koelreuteria Panicu*), tulip tree (*Lirodendron Tulipifera*), borage (*Borago Officialis*), anise hyssop (*Agastache Foeniculum*), buckwheat (*Fagopyrum Esculentum*), catnip (*Nepeta Cataria*), garden hyssop (*Hyssop Officialis*), English lavender (*Lavendula Augustifolia*), blue salvia (*Salvia Farinacea*), annual dragon head (*Draco*), tuberous vetchling (*Lathyrus Tuberosus*), French pussy willow (*Salix Caprea*), mountain mint (*Pycnanthemum Pilosum*), wild indigo (*Baptisia Australis*), Virginia waterleaf (*Hydrophyllum*), arrow leaf aster (*Aster Sagittifolius*), golden honey plant (*Actinomeris Alternfolia*), wild marjoram (*Origanum Vulgare*), Chapman honey plant (*Echinops Sphaerocephalus*), blue globe flower (*Echinops Vitro*), Jerusalem sage (*Phlomis Tuberosa*), chivirico (*Leonorus Cardiaca*), spider plant (*Cleome Spinosa*), and phacella (*Phacelia Tenacetifolia*).

The flora 13 and the bee colonies 14 are distributed on the basis of the following criteria:
1) the topography of the parcel of land 10 as well as the existing service roads 12;
2) minimizing the flying distance between the pasture and the bee colonies 14; and
3) assuring the amount of nectar available from the pasture is commensurate with the number of bees working the pasture.

According to the present invention the flora 13 and the bee colonies 14 are distributed in systematic patterns and relative numbers to optimize the aforementioned criteria. Two broad concepts are envisioned within the scope of the present invention.

First, the pasture may be arranged on a first piece of the land in such a manner as to facilitate the necessary maintenance of the pasture. In practice, it has been generally determined that a spacing of approximately twenty feet on center allows adequate access to each of the flowering flora 13. The bee colonies 14 are arranged on a second piece of the land in close proximity to the first piece in such a manner as to facilitate the necessary maintenance of the bee colonies 14. In practice, it has been generally determined that placement of the hives in well cleared areas facilitates access thereto for the purposes of maintaining the brood chamber as well as harvesting the honey. For example, placing the bee colonies 14 along an access road 11 further eases access to the bee colonies 14. By utilizing the first and second pieces of the parcel of the land 10 as thus described, access to the flowering flora 13 and the bee colonies 14 is eased, however a slight reduction in the quantity of honey extracted from each bee colony 14 per year may occur owing to the fact the bees consume greater quantities of nectar flying further distances between the pasture and the bee colonies 14.

Second, the pasture and the bee colonies 14 may be distributed such that at least one of the bee colonies 14 is proximately associated on a proportional basis with at least one of the flowering flora 13. The important aspect is the close proximity of bee colony to the pasture, thereby maximizing the honey produced by each bee colony 14 per year.

The honey which is collected according to the present invention is extracted from combs removed from the bee colonies 14. In a preferred embodiment of the present invention, the honey is extracted by any commonly known technique, e.g. with a centrifuge, at the extraction and distillation plant 20.

Figure 2:
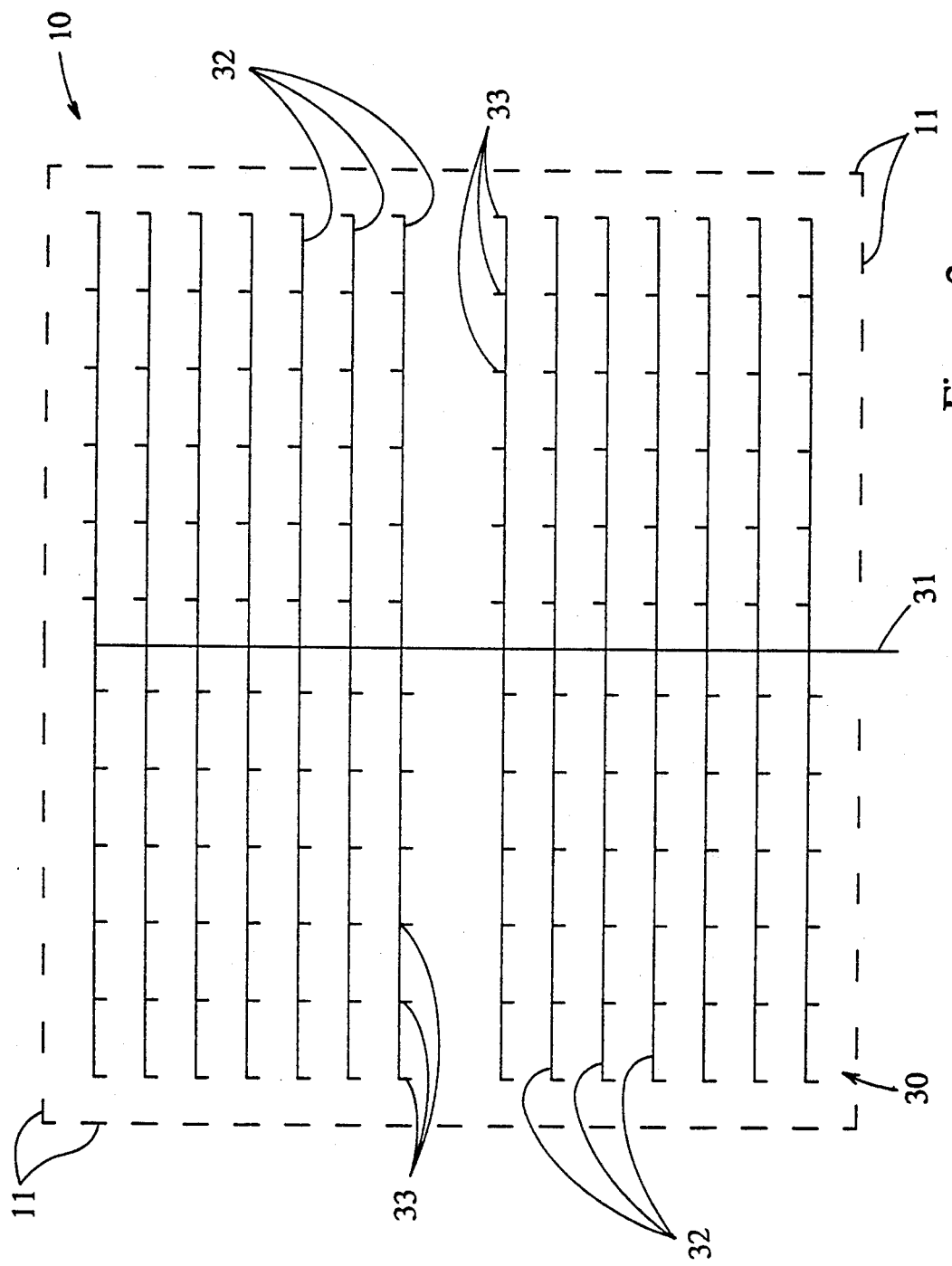
FIG. 2 shows a typical layout for irrigating the pasture shown in FIG. 1.

In certain climates where the rain fall is insufficient for optimum growth of the pasture, an irrigation system 30 as shown in FIG. 2 may be installed to augment the rain fall. In a known manner, the supply of water through the trunk lines 31, the branch lines 32 and the feeder lines 33 may be regulated individually o in groups. In a preferred embodiment of the present invention, water tanks 21 and pumps 22 for distributing the water are located at the extraction and distillation plant 20.

Fuel alcohol, ethanol, is obtained according to the present invention at the extraction and distillation plant 20. The honey provides a supply of liquid sugar which is readily converted to fuel alcohol by fermentation. Fermentation is caused to occur in the extraction and distillation plant 20 by:
1) adding water to the honey as necessary to lower the sugar concentration below 88% so as not to inhibit the growth of yeast cells;
2) adjusting the Ph to approximately 5.0, and adding ammonium sulfate and phosphates as necessary to assure an adequate supply of nitrogen and phosphorus as yeast nutrients; and
3) adding yeast to the honey for rapid fermentation into ethanol, usually within forty-eight hours.

A significant advantage of the present invention over fuel alcohol produced using grain as a raw material, is the elimination of several processing steps and the corresponding equipment necessary for accomplishing the eliminated steps. Specifically, according to the present invention, the process steps associated with growing and storing a seasonal grain, as well as converting the starchy grain into a sugar are eliminated. The corresponding equipment which is eliminated includes grain storage bins, grain mashing equipment, mash cooking equipment, mash drying equipment, as well as aeration and settling tanks.

Figure 3:
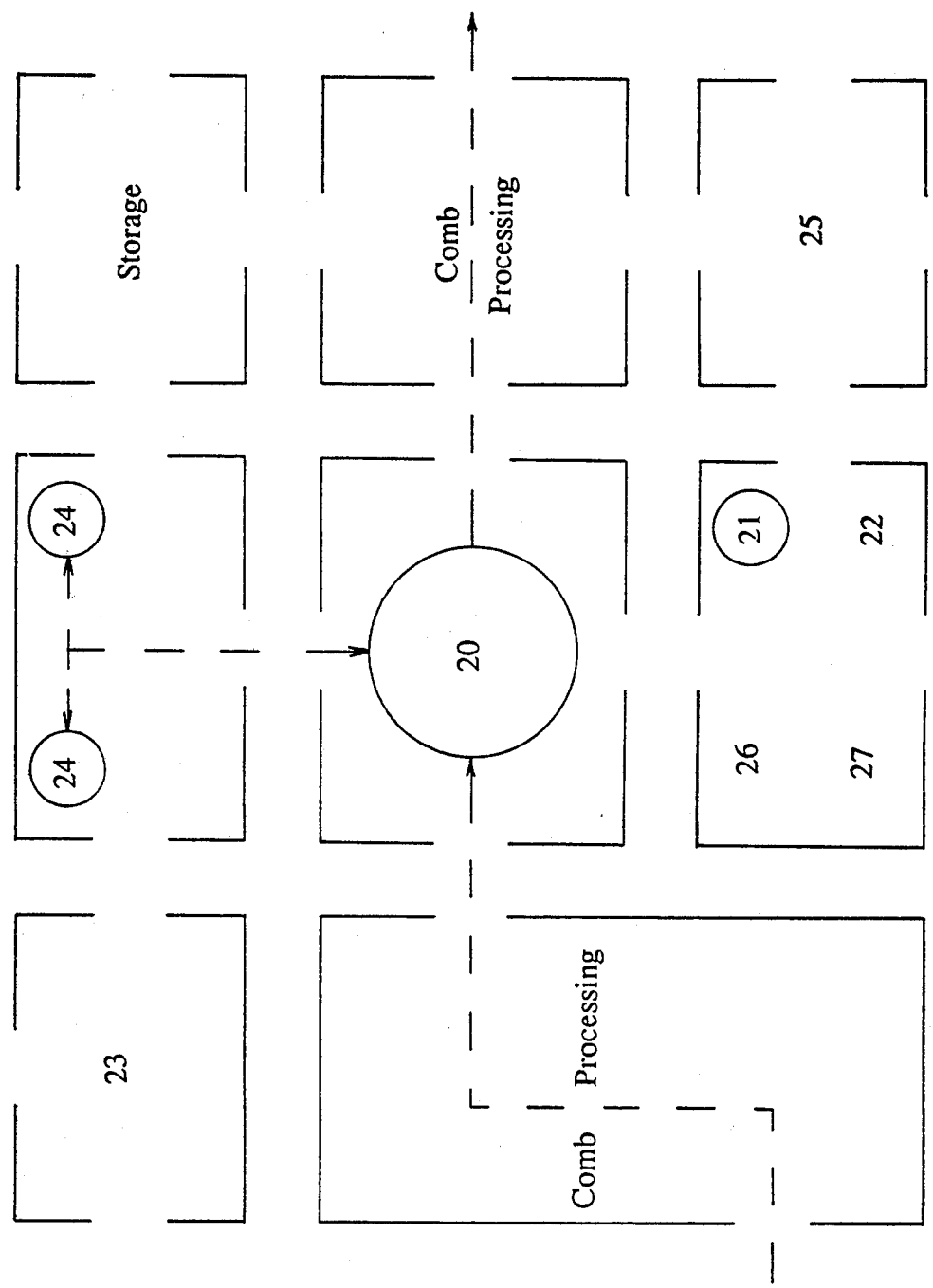
FIG. 3 shows a typical layout of a facility for converting honey to fuel alcohol which is remotely located with respect to the pasture shown in FIG. 1.

FIG. 3 shows a preferred embodiment according to the present invention wherein a non-fossil fuel power plant 23 for generating electricity, honey storage tanks 24, equipment repair facilities 25, even food storage facilities 26 and employee living quarters 27 are located at the extraction and distillation plant 20.

The present invention should not be construed as limited by any specific examples cited for the purpose of enhancing the foregoing description. The present invention is limited only by the scope and breadth of the appended claims which are supported by this disclosure.

What is claimed is:

1. A system of harvesting honey, comprising the steps of:
   clearing a selected area of land;
   massing a species of perennially flowering plant in said selected area according to a systematic pattern for a given terrain;
   introducing bee colonies according to a preselected pattern among the mass of flowering plant; and
   harvesting the honey at regular intervals year round.

* * * * *